US00PP27346P3

(12) United States Plant Patent
Danziger

(10) Patent No.: US PP27,346 P3
(45) Date of Patent: Nov. 1, 2016

(54) ***ANGELONIA* PLANT NAMED 'DALONDPINK'**

(50) Latin Name: *Angelonia angustifloria*
Varietal Denomination: DALONDPINK

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 37 days.

(21) Appl. No.: 14/544,750

(22) Filed: Feb. 12, 2015

(65) Prior Publication Data

US 2016/0242347 P1 Aug. 18, 2016

(51) Int. Cl.
*A01H 5/02* (2006.01)

(52) U.S. Cl.
USPC ..... Plt./404

(58) Field of Classification Search
USPC ..... Plt./404
See application file for complete search history.

*Primary Examiner* — Annette Para

(74) *Attorney, Agent, or Firm* — Cassandra Bright

(57) ABSTRACT

A new and distinct *Angelonia* cultivar named 'DALONDPINK' is disclosed, characterized by an upright and free branching plant habit, large dark pink flowers and good garden performance. The new variety is an *Angelonia*, normally produced as an outdoor garden or container plant.

2 Drawing Sheets

Figure 1:
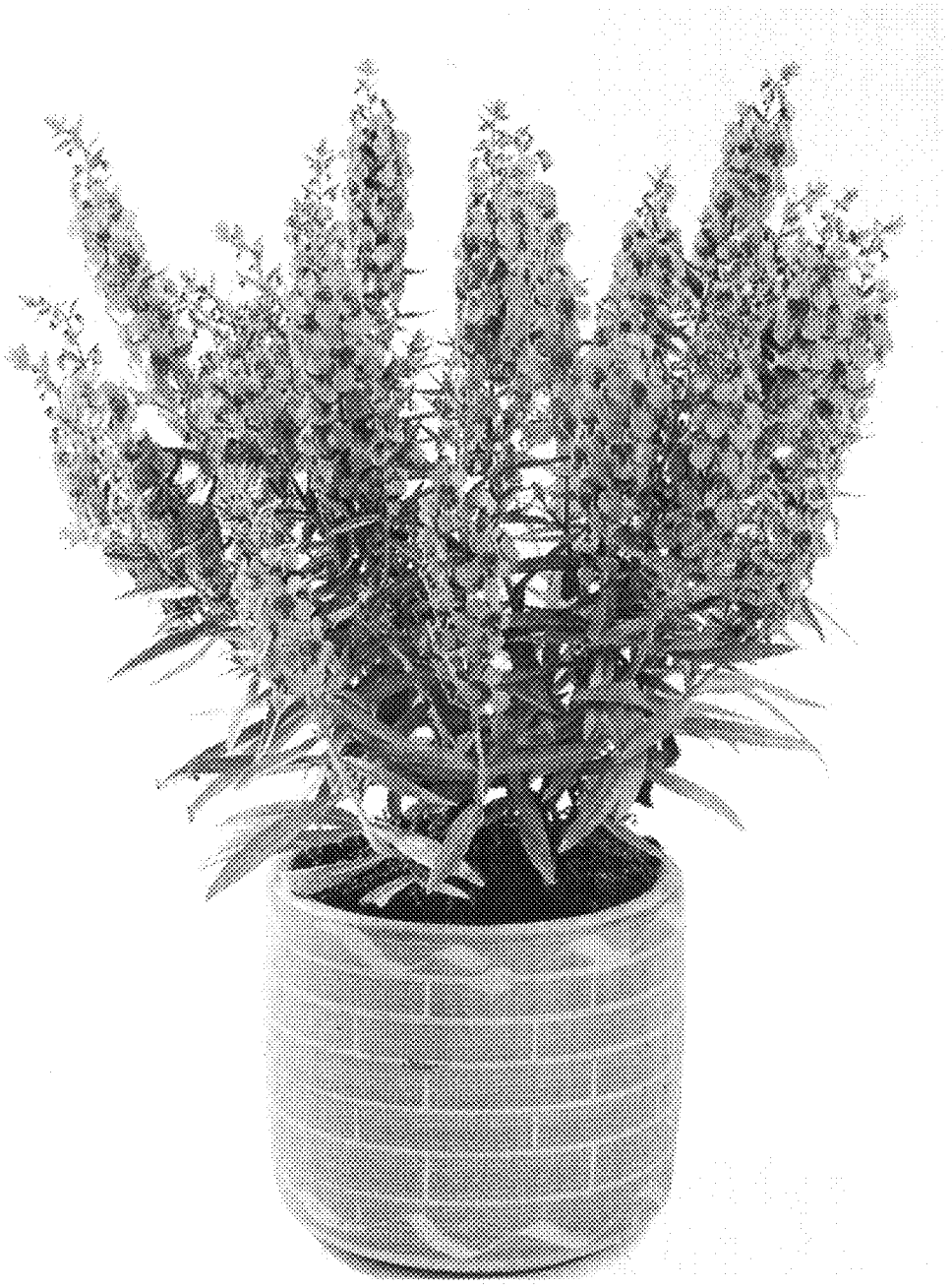

Latin name of the genus and species: *Angelonia angustifloria.*

Variety denomination: 'DALONDPINK'.

BACKGROUND OF THE INVENTION

The new *Angelonia* cultivar is a product of a planned breeding program conducted by the inventor, Gavriel Danziger, in Moshav Mishmar Hashiva, Israel. The objective of the breeding program was to produce new *Angelonia* varieties for ornamental commercial applications. The crossing resulting in this new variety was made during May of 2010.

The seed parent is the, unpatented, proprietary variety referred to as *Angelonia* 'AL 59'. The pollen parent is the unpatented, propriety variety referred to as *Angelonia* 'AL 516'. The new variety was discovered in April of 2011 by the inventor in a group of seedlings resulting from the 2010 crossing, in a research greenhouse in Moshav Mishmar Hashiva, Israel.

Asexual reproduction of the new cultivar was performed by vegetative tip cuttings. This was first performed at a research greenhouse in Moshav Mishmar Hashiva, Israel in May of 2011 and has shown that the unique features of this cultivar are stable and reproduced true to type in multiple successive generations.

SUMMARY OF THE INVENTION

The cultivar 'DALONDPINK' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DALONDPINK' These characteristics in combination distinguish 'DALONDPINK' as a new and distinct *Angelonia* cultivar:

1. Upright plant habit.
2. Freely branching habit
3. Large dark pink colored flowers.
4. Good garden performance.

Plants of the new cultivar 'DALONDPINK' are similar to plants of the seed parent, *Angelonia* 'AL 59' in most horticultural characteristics, however, plants of the new cultivar 'DALONDPINK' differ in the following;

1. Flower color of the parent is lighter.
2. Flower size of the parent is smaller.

Plants of the new cultivar 'DALONDPINK' are similar to plants of the pollen parent, *Angelonia* 'AL 516' in most horticultural characteristics, however, plants of the new cultivar 'DALONDPINK' differ in the following;

1. Flower color of the parent is lighter.
2. Growth habit of the parent is more compact.

COMMERCIAL COMPARISON

Plants of the new cultivar 'DALONDPINK' are comparable to the unpatented, commercial variety *Angelonia* 'DALON10'. The two *Angelonia* varieties are similar in most horticultural characteristics; however, the new variety 'DALONDPINK' differs in the following:

1. Darker flower color.
2. Larger flower size.

Plants of the new cultivar 'DALONDPINK' can also be comparable to the unpatented commercial variety *Angelonia* 'DALON12', U.S. application Ser. No. 13/986,280. The two *Angelonia* varieties are similar in most horticultural characteristics; however, the new variety 'DALONDPINK' differs in the following:

1. Flower color of the new variety is dark pink; the flower color of the comparator is white.

BRIEF DESCRIPTION OF THE PHOTOGRAPHS

The accompanying photograph in FIG. 1 illustrates in full color a typical plant of 'DALONDPINK' grown in a greenhouse, in a 13 cm pot. Age of the plant photographed is approximately 60 days from a rooted cutting.

Figure 2:
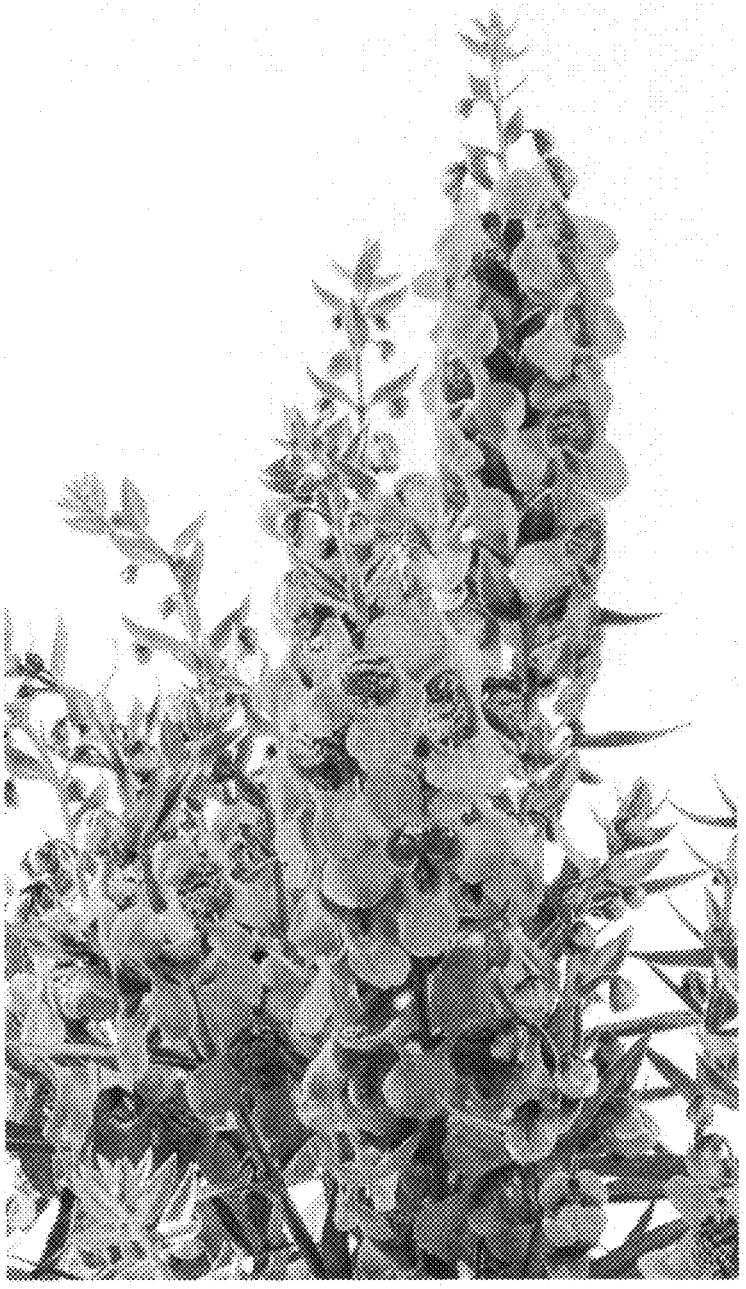

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DALONDPINK' plants grown in a greenhouse, in Moshav Mishmar Hashiva, Israel. The growing temperature ranged from 20° C. to 30° C. during the day and from 15° C. to 25° C. during the night. General light conditions are bright, normal sunlight. Measurements and numerical values represent averages of typical plant types. Botanical classification: *Angelonia* 'DALONDPINK'.

PROPAGATION

Type of propagation typically used: Vegetative tip cuttings.
Time to initiate roots: 10-15 days.
Root description: Fibrous, well branched.

PLANT

Age of plant described: Approximately 70 days.
Container size of the plant described: 13 cm.
Growth habit: Erect.
Height:
- *To top of foliage.*—20 cm.
- *To top of flowers.*—30 cm.

Plant spread: 30 cm.
Growth rate: Fast.
Branching characteristics: Medium.
Length of primary lateral branches: 30 cm.
Diameter of lateral branches: 0.5 cm.
Quantity of primary lateral branches: 6-8.
Characteristics of primary lateral branches:
- *Form.*—Round.
- *Diameter.*—0.5 cm.
- *Color.*—Near RHS Green 137B.
- *Texture.*—Puberulous.
- *Strength.*—Somewhat rigid.

Internode length: Average 2.5 cm.

FOLIAGE

Leaf:
- *Arrangement.*—Opposite.
- *Quantity.*—Approximately 20-25 per branch.
- *Average length.*—3-9 cm.
- *Average width.*—1.5 cm.
- *Shape of blade.*—Lance.
- *Apex.*—Sharply pointed.
- *Base.*—Wedge Shaped.
- *Margin.*—Scalloped.
- *Texture of top surface.*—Smooth.
- *Texture of bottom surface.*—Smooth.
- *Pubescence.*—No.
- *Aspect.*—50°.
- *Color.*—Young foliage upper side: Near RHS Green 143A. Young foliage under side: Near RHS Green 143B. Mature foliage upper side: Near RHS Green N137A. Mature foliage under side: Near RHS Green 138A.
- *Venation.*—Type: Pinnate. Venation color upper side: Near RHS Yellow-Green 144B. Venation color under side: Near RHS Yellow-Green 144C.
- *Petiole.*—None.

FLOWER

Natural flowering season: Spring, Summer and Autumn.
Days to flowering from rooted cutting: 60.
Inflorescence and flower type and habit: Panicle.
Rate of flower opening: 7 to 14 days from bud to fully opened flower.
Flower longevity on plant: 5-8 days.
Persistent or self-cleaning: Self Cleaning.
Bud:
- *Shape.*—Round.
- *Length.*—0.5 cm.
- *Diameter.*—0.5 cm.
- *Color.*—Near RHS Green-Yellow 1 C.

Flower size:
- *Diameter.*—3 cm.
- *Length.*—2.8 cm.

Petals:
- *Length.*—1 cm.
- *Diameter.*—1.2 cm.
- *Quantity.*—5.
- *Texture.*—Smooth.
- *Apex.*—Rounded.
- *Color.*—When opening: Upper surface: Near RHS Red-purple 70 B. Lower surface: Near RHS Red-purple 70 B. Fully opened: Upper surface: Near RHS Red-purple 70 B. Lower surface: Near RHS Red-purple 70 B.

Sepals:
- *Quantity per flower.*—5.
- *Shape.*—Ovate.
- *Length.*—0.5 cm.
- *Width.*—0.3 cm.
- *Apex.*—Acute.
- *Base.*—Attenuate.
- *Margin.*—Entire.
- *Texture.*—Puberulous.
- *Color.*—Near RHS Brown 200A.

Pedicel:
- *Length.*—1.5 cm.
- *Diameter.*—0.1 cm.
- *Color.*—Near RHS Green N137A.

Fragrance: Delicate.

REPRODUCTIVE ORGANS

Stamens:
- *Number.*—4.
- *Filament length.*—3 mm.

Anthers:
- *Shape.*—Eliptic.
- *Length.*—2 mm.
- *Color.*—Near RHS Greyed-orange 164 C.

Pollen:
- *Color.*—Near RHS White 155D.
- *Quantity.*—Moderate.

Pistil:

*Number.*—1.

*Length.*—0.3 cm.

*Style.*—Length: 0.4 cm. Color: Near RHS Violet 84D.

*Stigma.*—Shape: Awnlike. Color: Near RHS Violet 84D.

OTHER CHARACTERISTICS

Seeds and fruits: Not always produced, if present, round capsule about 0.3-0.5 cm long with 50-75 seeds. Dark brown color not accurately measured with RHS chart.

Disease/pest resistance: Neither resistance nor susceptibility to the normal diseases and pests of *Angelonia* have been observed. Pests common to *Angelonia* include Aphids and thrips. Typical diseases are *Botrytis* and *Pythium.*

Temperature tolerance: 10°-35° Celsuis.

What is claimed is:

1. A new and distinct cultivar of *Angelonia* plant named 'DALONDPINK' as herein illustrated and described.

* * * * *